(12) United States Patent
Koka et al.

(10) Patent No.: US 10,639,475 B2
(45) Date of Patent: May 5, 2020

(54) SYSTEMS AND METHODS FOR USING AN EVOKED RESPONSE TO DETERMINE A BEHAVIORAL AUDIOGRAM VALUE

(71) Applicants: Kanthaiah Koka, Valencia, CA (US); Leonid M. Litvak, Los Angeles, CA (US); ADVANCED BIONICS AG, Staefa (CH)

(72) Inventors: Kanthaiah Koka, Valencia, CA (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 16/080,367

(22) PCT Filed: Feb. 29, 2016

(86) PCT No.: PCT/US2016/020140
§ 371 (c)(1),
(2) Date: Aug. 28, 2018

(87) PCT Pub. No.: WO2017/151105
PCT Pub. Date: Sep. 8, 2017

(65) Prior Publication Data
US 2019/0046796 A1 Feb. 14, 2019

(51) Int. Cl.
*H04R 29/00* (2006.01)
*A61N 1/36* (2006.01)
(Continued)

(52) U.S. Cl.
CPC ...... *A61N 1/36038* (2017.08); *A61B 5/04845* (2013.01); *A61B 5/125* (2013.01);
(Continued)

(58) Field of Classification Search
USPC .......................................................... 381/60
See application file for complete search history.

(56) References Cited

U.S. PATENT DOCUMENTS 9,008,340 B2 4/2015 Ku et al.
9,025,800 B2 5/2015 Kidmose et al.
(Continued)

FOREIGN PATENT DOCUMENTS

| WO | 2015/130318 | 9/2015 |
| WO | 2015/161175 | 10/2015 |
| WO | 2017/182931 | 10/2017 |

OTHER PUBLICATIONS

International Search Report and Written Opinion received in International Application No. PCT/US16/020140, dated Nov. 21, 2016.

*Primary Examiner* — Quoc D Tran
(74) *Attorney, Agent, or Firm* — ALG Intellectual Property, LLC

(57) ABSTRACT

An exemplary behavioral audiogram generation system 1) determines a noise floor within the cochlea of a patient, 2) presents, by way of a loudspeaker, acoustic stimulation having a predetermined frequency and a predetermined amplitude to the patient, 3) detects an evoked response that occurs in response to the acoustic stimulation, 4) determines an amplitude of the evoked response that occurs in response to the acoustic stimulation, and 5) determines, based on the amplitude of the evoked response, on the predetermined amplitude of the acoustic stimulation, and on the noise floor, a behavioral audiogram value for the patient that corresponds to the predetermined frequency.

20 Claims, 12 Drawing Sheets

(51) Int. Cl.
  *A61B 5/0484* (2006.01)
  *A61B 5/12* (2006.01)
  *A61N 1/05* (2006.01)
  *A61N 1/08* (2006.01)
  *H04R 3/00* (2006.01)
  *A61B 5/04* (2006.01)

(52) U.S. Cl.
  CPC ............ *A61N 1/0541* (2013.01); *A61N 1/08* (2013.01); *A61N 1/36036* (2017.08); *H04R 3/00* (2013.01); *A61B 5/04001* (2013.01)

(56) References Cited

U.S. PATENT DOCUMENTS

| | | | |
|---|---|---|---|
| 2004/0064066 A1* | 4/2004 | John | A61B 5/04845 600/559 |
| 2005/0261748 A1* | 11/2005 | Van Dijk | A61N 1/36036 607/57 |
| 2008/0249589 A1 | 10/2008 | Cornejo Cruz et al. | |
| 2012/0245655 A1* | 9/2012 | Spitzer | A61B 5/125 607/57 |
| 2015/0016647 A1 | 1/2015 | Segovia Martinez et al. | |
| 2015/0215710 A1* | 7/2015 | Francart | H04R 25/356 381/326 |
| 2015/0341731 A1* | 11/2015 | Polak | H04R 25/70 600/25 |
| 2016/0045749 A1 | 2/2016 | James et al. | |
| 2016/0096020 A1* | 4/2016 | Smith | A61N 1/0541 600/25 |
| 2016/0151629 A1* | 6/2016 | Chalupper | A61N 1/36036 607/57 |

* cited by examiner

SYSTEMS AND METHODS FOR USING AN EVOKED RESPONSE TO DETERMINE A BEHAVIORAL AUDIOGRAM VALUE

BACKGROUND INFORMATION

Behavioral audiograms provide information regarding the residual hearing ability and/or hearing thresholds of hearing loss patients. For example, a behavioral audiogram for a particular hearing loss patient may indicate the softest (e.g., lowest amplitude) sounds that the patient is able to hear at a variety of different frequencies. Hence, it may be beneficial to obtain a behavioral audiogram for a hearing loss patient that uses an auditory prosthesis system (e.g., a cochlear implant system or an electro-acoustic stimulation ("EAS") system) in order to optimally program or fit the auditory prosthesis system to the patient.

Conventional techniques for obtaining a behavioral audiogram are subjective and depend on feedback provided by the hearing loss patient. Unfortunately, this makes it difficult or impossible to obtain a behavioral audiogram for a nonresponsive patient (e.g., a pediatric patient, an unconscious patient, etc.).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
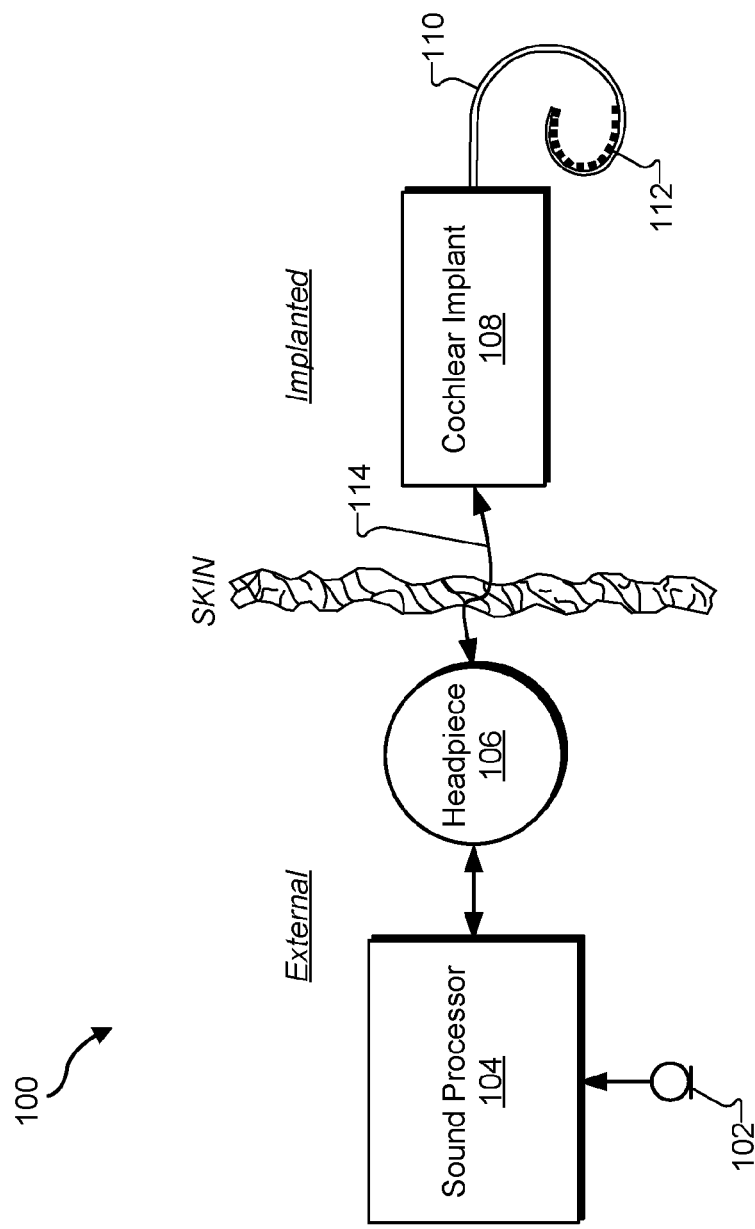
FIG. 1 illustrates an exemplary auditory prosthesis system according to principles described herein.

Systems and methods for using an evoked response to determine a behavioral audiogram value are disclosed herein. For example, an exemplary behavioral audiogram generation system implemented by at least one physical computing device may determine a noise floor within a cochlea of a patient. The behavioral audiogram generation system may present, by way of a loudspeaker, acoustic stimulation having a predetermined frequency and a predetermined amplitude to the patient. The behavioral audiogram generation system may then detect an evoked response that occurs in response to the acoustic stimulation, and determine an amplitude of the evoked response at the predetermined frequency. The behavioral audiogram generation system may then determine, based on the amplitude of the evoked response, on the predetermined amplitude of the acoustic stimulation, and on the noise floor, a behavioral audiogram value for the patient that corresponds to the predetermined frequency.

Various benefits may be realized by the systems and methods described herein. By facilitating objective measurement of a patient's behavioral audiogram values, the systems and methods described herein may improve the accuracy, efficiency, and/or comfort of a fitting and/or an adjustment of an auditory prosthesis system associated with the patient. For example, a health care professional may be able to objectively measure residual hearing in non-responsive patients such as non-verbal children or unconscious patients (e.g., patients who have not yet awakened from an implantation surgery). This may allow the health care professional to properly fit and/or adjust a patient's auditory prosthesis system using objective measurements of the patient's behavioral audiogram values without (or in concert with) subjective feedback from the patient.

As used herein, an "evoked response" refers to an intra-cochlear hair-cell response (i.e., cochlear microphonics), a neural response (e.g., an auditory nerve response, a brainstem response, a compound action potential), an electrocochlear potential, and/or any other type of neural or physiological response that may occur within a patient in response to application of acoustic stimulation to the patient.

As used herein, "noise" refers to any disturbance in a measurement system (e.g., the behavioral audiogram generation system described herein) that interferes with and/or prevents reception of a desired signal. A "noise floor" is a measure of signal created from the sum of noise sources and/or other unwanted signals within the measurement system. In general, a measurement system may be unable to distinguish a signal with a lower signal strength than the measurement system's noise floor from the noise sources comprising the noise floor. Thus, the measurement system may not be capable of accurately and/or precisely perceiving a signal with a signal strength lower than the measurement system's noise floor as distinct from the noise sources comprising the measurement system's noise floor. Examples of determining a noise floor within a cochlea of a patient will be described in detail below.

As used herein, a "behavioral audiogram value" (also called a "threshold value") refers to the lowest amplitude (e.g., in dB hearing level ("HL"), which refers to a logarithmic scale of sound intensity expressed in decibels and referenced to average normal hearing) at which a patient may detect or perceive a presentation of a frequency-specific tone. In some examples, a behavioral audiogram value may refer to the lowest amplitude at which a patient may detect multiple presentations of a frequency-specific tone a predetermined percentage of time (e.g., fifty percent of the time). For example, if a patient is able to detect a 1,000 Hz tone at 45 dB HL fifty percent of the time, but cannot detect a 1,000 Hz tone at 44 dB HL fifty percent of the time, the patient's behavioral audiogram value corresponding to a frequency of 1,000 Hz may be designated as 45 dB HL.

FIG. 1 illustrates an exemplary auditory prosthesis system 100. As shown, auditory prosthesis system 100 may include various components configured to be located external to a user including, but not limited to, a microphone 102, a sound processor 104, and a headpiece 106. Auditory prosthesis system 100 may further include various components configured to be implanted within the user including, but not limited to, a cochlear implant 108 and a lead 110 (also referred to as an intracochlear electrode array) with a plurality of electrodes 112 disposed thereon. As will be described in more detail below, additional or alternative components may be included within auditory prosthesis system 100 as may serve a particular implementation. The components shown in FIG. 1 will now be described in more detail.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the user. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an EAS sound processor included in an EAS system configured to provide electrical and acoustic stimulation to a user.

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bidirectional communication link and/or one or more dedicated unidirectional communication links. In some examples, sound processor 104 may execute and operate in accordance with a sound processing program that has been loaded into memory contained within sound processor 104.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the user's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bidirectional communication link and/or one or more dedicated unidirectional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a user and configured to apply stimulation to one or more stimulation sites located along an auditory pathway of a user.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the user via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") by way of multiple electrodes 112.

Figure 2:
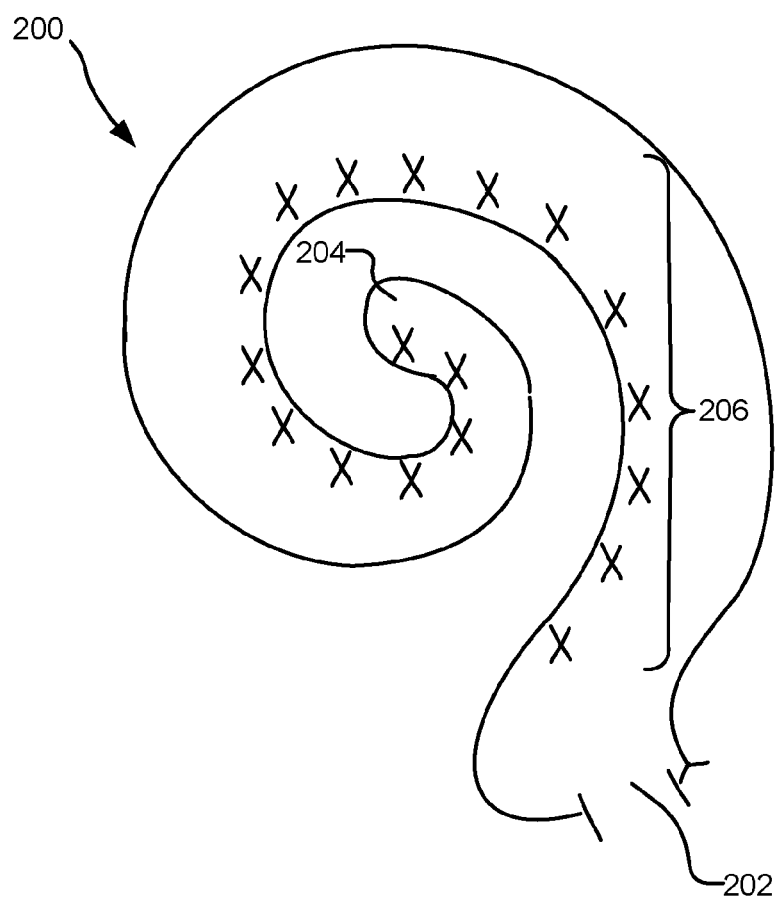
FIG. 2 illustrates a schematic structure of the human cochlea according to principles described herein.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Auditory prosthesis system 100 may therefore be configured to apply electrical stimulation to different locations within the cochlea 200 (e.g., different locations along the auditory nerve tissue 206) to provide a sensation of hearing.

The auditory prosthesis system 100 illustrated in FIG. 1 may be referred to as a cochlear implant system because sound processor 104 is configured to direct cochlear implant 108 to generate and apply electrical stimulation representative of audio content (e.g., one or more audio signals) to one or more stimulation sites within the patient by way of one or more of electrodes 112.

Figure 3:
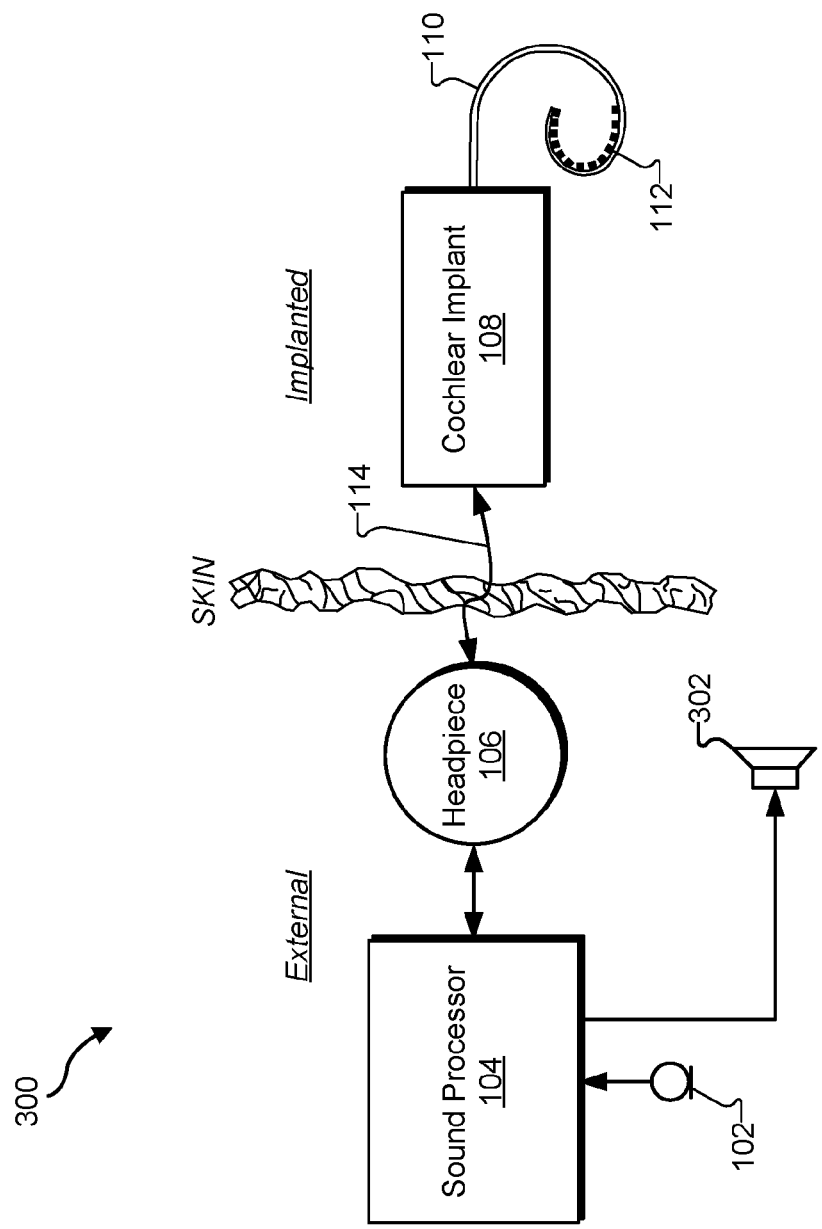
FIG. 3 illustrates an exemplary implementation of the auditory prosthesis system of FIG. 1 according to principles described herein.

FIG. 3 illustrates an exemplary implementation 300 of auditory prosthesis system 100 in which auditory prosthesis system 100 is further configured to provide acoustic stimulation to the patient. Hence, implementation 300 shown in FIG. 3 may be referred to as an EAS system.

As shown, implementation 300 may further include a loudspeaker 302 (also referred to as a "receiver"). Loudspeaker 302 may be in communication with an ear of the patient (e.g., located at an entrance or within the ear canal of the patient). In this configuration, sound processor 104 (which, in implementation 300, may be referred to as an "EAS sound processor") may be configured to direct loudspeaker 302 to apply acoustic stimulation representative of audio content included in relatively low frequency bands (e.g., below 1000 Hz) to the patient and cochlear implant 108 to apply electrical stimulation representative of audio content included in relatively high frequency bands (e.g., above 1000 Hz) to one or more stimulation sites within the patient by way of one or more of intracochlear electrodes 112.

In some examples, a programming system separate from (i.e., not included within) auditory prosthesis system 100 may be selectively and communicatively coupled to sound processor 104 in order to perform one or more programming or fitting operations with respect to auditory prosthesis system 100.

Figure 4:
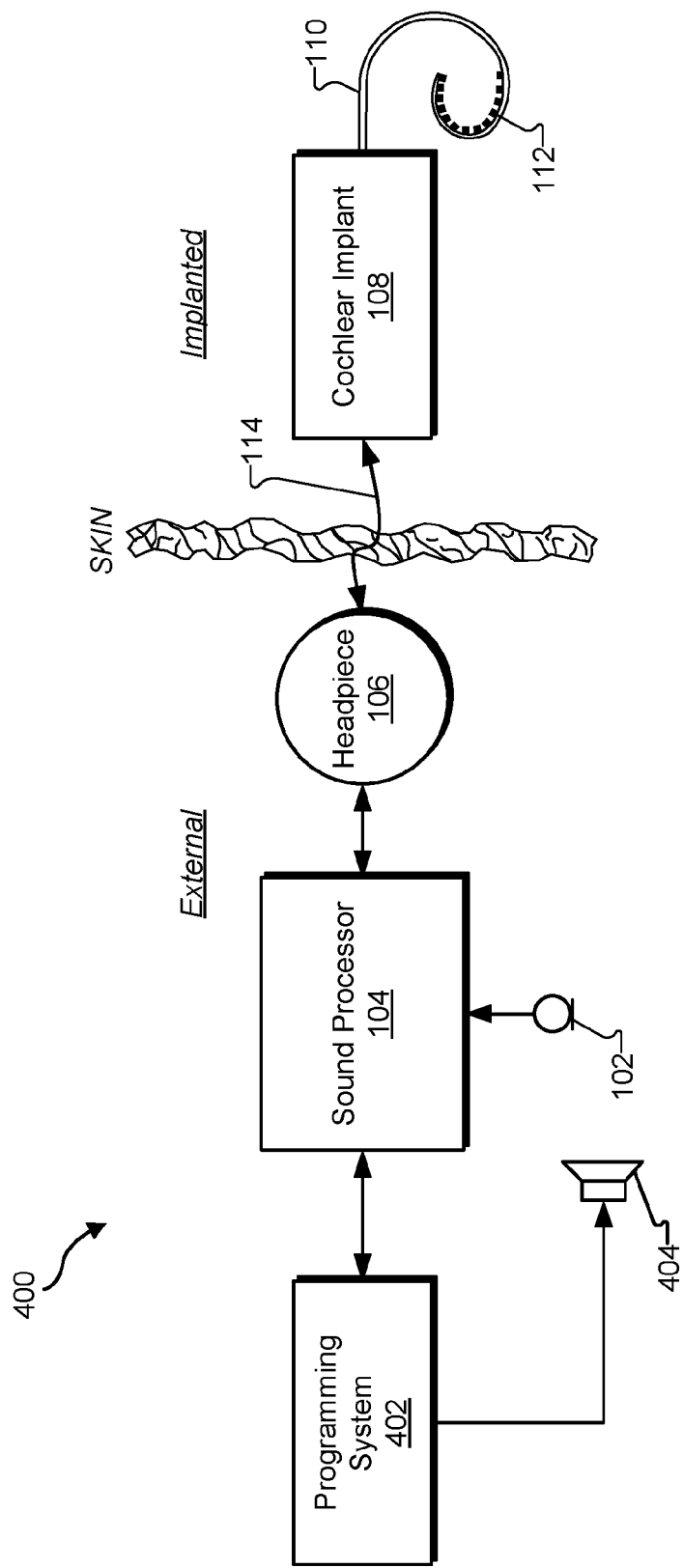
FIG. 4 shows an exemplary configuration in which a programming system is communicatively coupled to a sound processor according to principles described herein.

To illustrate, FIG. 4 shows an exemplary configuration 400 in which a programming system 402 is communicatively coupled to sound processor 104.

Programming system 402 may be implemented by any suitable combination of physical computing and communication devices including, but not limited to, a fitting station or device, a programming device, a personal computer, a laptop computer, a handheld device, a mobile device (e.g., a mobile phone), a clinician's programming interface ("CPI") device, and/or any other suitable component as may serve a particular implementation. In some examples, programming system 402 may provide one or more graphical user interfaces ("GUIs") (e.g., by displaying the one or more GUIs by way of a display screen) with which a clinician or other user may interact.

As shown, configuration 400 may further include a loudspeaker 404 (also referred to as a "receiver"). Loudspeaker 404 may be in communication with an ear of the patient (e.g., located at an entrance or within the ear canal of the patient). In this configuration, programming system 402 may be configured to direct receiver loudspeaker 404 to apply acoustic stimulation representative of audio content included in relatively low frequency bands (e.g., below 1000 Hz) to the patient and cochlear implant 108 to apply electrical stimulation representative of audio content included in relatively high frequency bands (e.g., above 1000 Hz) to one or more stimulation sites within the patient by way of one or more of intracochlear electrodes 112.

Figure 5:
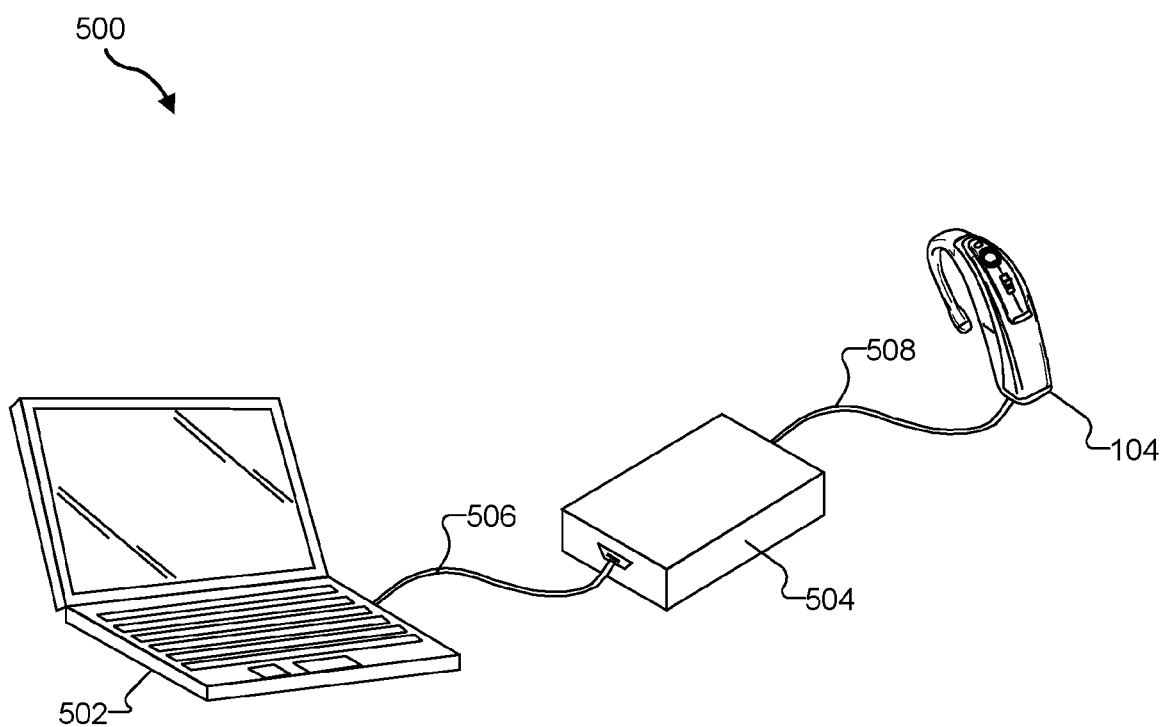
FIG. 5 illustrates an exemplary implementation of a programming system according to principles described herein.

FIG. 5 illustrates an exemplary configuration 500 in which programming system 402 is implemented by a computing device 502 and a CPI device 504. As shown, computing device 502 may be selectively and communicatively coupled to CPI device 504 by way of a cable 506. Likewise, CPI device 504 may be selectively and communicatively coupled to sound processor 104 by way of a cable 508. Cables 506 and 508 may each include any suitable type of cable that facilitates transmission of digital data between computing device 502 and sound processor 104. For example, cable 506 may include a universal serial bus ("USB") cable and cable 508 may include any type of cable configured to connect to a programming port included in sound processor 104.

Configuration 500 corresponds to a unilateral cochlear implant system (i.e., there is a single sound processor 104 that corresponds to one ear of the patient). It will be recognized that the systems and methods described herein may be applied to a bilateral cochlear implant system in which separate sound processors are associated with each ear of the patient. In these instances, programming system 402 may be implemented by two CPI devices, each associated with one of the sound processors.

Figure 6:
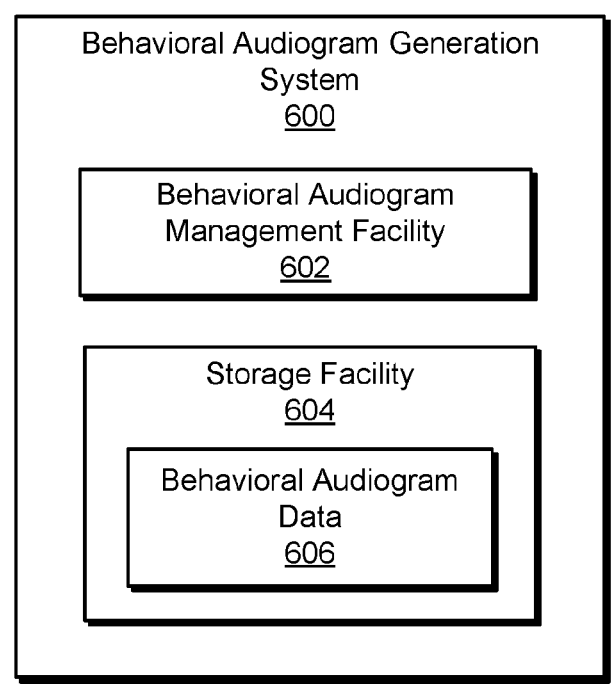
FIG. 6 illustrates exemplary components of a behavioral audiogram generation system according to principles described herein.

FIG. 6 illustrates exemplary components of a behavioral audiogram generation system 600 ("system 600"). System 600 may be configured to generate a behavioral audiogram for a patient and may be implemented entirely by sound processor 104, entirely by programming system 402, or by a combination of sound processor 104 and programming system 402.

As shown, system 600 may include a behavioral audiogram management facility 602 ("management facility 602") and a storage facility 604, which may be in communication with one another using any suitable communication technologies. Storage facility 604 may maintain behavioral audiogram data 606 generated and/or used by management facility 602. Storage facility 604 may maintain additional or alternative data as may serve a particular implementation.

Management facility 602 may perform various operations associated with using detected evoked responses to determine behavioral audiogram values for a patient. Exemplary operations that may be performed by management facility 602 will now be described.

In some examples, management facility 602 may determine a noise floor within a cochlea of a patient. As will be described below, the determined noise floor may be used by management facility 602 to determine a behavioral audiogram value for the patient.

Management facility 602 may determine the noise floor in any suitable way. For example, management facility 602 may determine the noise floor by abstaining from presenting acoustic stimulation to the patient for a predetermined time period. During this time period during which no acoustic stimulation is being presented to the patient, management facility 602 may use an electrode (e.g., the same electrode used to detect evoked responses) to record a signal. Because this signal is recorded while no acoustic stimulation is being presented to the patient, it may only include a noise component (as opposed to both a noise component and an evoked response component that may be included in a signal recorded by the electrode in the presence of acoustic stimulation). Management facility 602 may determine an amplitude (e.g., an average amplitude over the predetermined time period) of the recorded signal and designate the determined amplitude as the noise floor.

Management facility 602 may employ one or more signal processing techniques to improve the accuracy of the determined noise floor. For example, management facility 602 may use signal averaging to adjust (e.g., reduce) the noise floor. For example, management facility 602 may detect multiple evoked responses that occur in response to acoustic stimulation (e.g., by repeatedly applying the acoustic stimulation and detecting an evoked response that occurs in response to each instance of acoustic stimulation). Management facility 602 may determine an average signal-to-noise ratio of the evoked responses and use the average signal-to-noise ratio to adjust the noise floor.

Additionally or alternatively, management facility 602 may determine the noise floor within a cochlea of a patient by receiving data representative of the noise floor from a source external to system 600. For example, the data representative of the noise floor may be received from a computing device not included in system 600. Additionally or alternatively, the data representative of the noise floor may be provided by a user of system 600 (e.g., by way of a user interface provided by system 600).

In some examples, the data representative of the noise floor may not necessarily be representative of the actual noise floor within the cochlea. For example, the data representative of the noise floor may be representative of an average of noise floors measured within cochleas of a plurality of other patients, an estimate of the noise floor within the cochlea of the patient, a predetermined threshold value not necessarily representative of an actual noise floor, and/or any other type of data as may serve a particular implementation. In some examples, the data representative of the noise floor may be frequency specific. For example, the data representative of the noise floor may include different values for different frequencies.

In order to determine a behavioral audiogram value that corresponds to a predetermined frequency, management facility 602 may present, by way of a loudspeaker, acoustic stimulation that has the predetermined frequency to the patient. For example, to determine a behavioral audiogram value for a frequency of 750 Hz, management facility 602 may present, by way of a loudspeaker, acoustic stimulation that has a frequency of 750 Hz to the patient. The acoustic stimulation may also have a predetermined amplitude. The predetermined amplitude may, for example, include an amplitude within a predetermined amplitude range of human hearing (e.g., 50 dB HL).

Management facility 602 may present the acoustic stimulation to the patient in any suitable way. For example, if management facility 602 is implemented by a sound processor (e.g., sound processor 104) included in an EAS system, the sound processor may present the acoustic stimulation by way of a loudspeaker (e.g., loudspeaker 302) that is physically and communicatively coupled to the sound processor. Alternatively, if management facility 602 is implemented by a programming system (e.g., programming system 402) separate from an auditory prosthesis system, the programming system may present the acoustic stimulation by way of a loudspeaker (e.g., loudspeaker 404) that is physically and communicatively coupled to the programming system.

Management facility 602 may detect an evoked response that occurs in response to the acoustic stimulation. Management facility 602 may detect the evoked response in any suitable manner. For example, an intracochlear hair-cell response may be detected using one or more electrodes positioned within the cochlea (e.g., one or more of electrodes 112), one or more electrodes positioned within the round window, one or more intraneural electrodes (i.e., one or more electrodes positioned within the auditory nerve), and/or one or more electrodes positioned at any other suitable location relatively near the cochlea. Likewise, an auditory nerve response and/or a compound action potential may be detected using one or more electrodes positioned within or near the cochlea. It will be recognized that the electrodes used to detect the evoked response may be disposed on a lead that has been inserted into the cochlea (e.g., lead 110) and/or on a lead that has been positioned at any other suitable location within the patient.

Additionally or alternatively, one or more electrodes located external to the patient may be used to detect an evoked response. For example, a brainstem response may be detected using one or more non-invasive electrodes that have been affixed externally to the head of the patient. The one or more externally located electrodes may be communicatively coupled to system 600 in any suitable manner. For example, the one or more externally located electrodes may be communicatively coupled directly to sound processor 104 and/or to programming system 402.

As mentioned above, management facility 602 may use the same one or more electrodes to detect the evoked response that are used to record the signal used to determine the noise floor.

In some examples, if management facility 602 is implemented by a sound processor (e.g., sound processor 104) included in an EAS system, the sound processor may detect the evoked response by wirelessly receiving a signal representative of the evoked response by way of a cochlear implant (e.g., cochlear implant 108) included in the EAS system. Alternatively, if management facility 602 is implemented by a programming system (e.g., programming system 402) communicatively coupled to a sound processor (e.g., sound processor 104) included in a cochlear implant system, the programming system may detect the evoked response by receiving a signal representative of the evoked response from the sound processor, which receives the signal from a cochlear implant (e.g., cochlear implant 108) included in the cochlear implant system.

Management facility 602 may determine an amplitude of the evoked response that occurs in response to the acoustic stimulation. Management facility 602 may determine the amplitude of the evoked response in any suitable way. For example, management facility 602 may determine an average amplitude of the evoked response over a predetermined time period and designate the average amplitude as the amplitude of the evoked response. As another example, management facility 602 may identify a peak amplitude of the evoked response and designate the peak amplitude as the amplitude of the evoked response.

Management facility 602 may use the amplitude of the evoked response, the predetermined amplitude of the acoustic stimulation, and the determined noise floor to determine a behavioral audiogram value for the patient and that corresponds to the predetermined frequency of the acoustic stimulation. Various manners in which the behavioral audiogram value may be determined will now be described.

In some examples, management facility 602 may determine the behavioral audiogram value using a single stimulus amplitude. In other words, management facility 602 may only have to apply a single instance of acoustic stimulation having a single predetermined amplitude in order to acquire information sufficient for determining the behavioral audiogram value. As will be illustrated below, this is because a substantially linear relationship exists between amplitudes of acoustic stimuli that each have the same predetermined frequency and amplitudes of evoked responses that occur in response to the presented acoustic stimuli. Hence, management facility 602 may determine the behavioral audiogram value using a single stimulus amplitude in accordance with a linear approximation heuristic.

Figure 7:
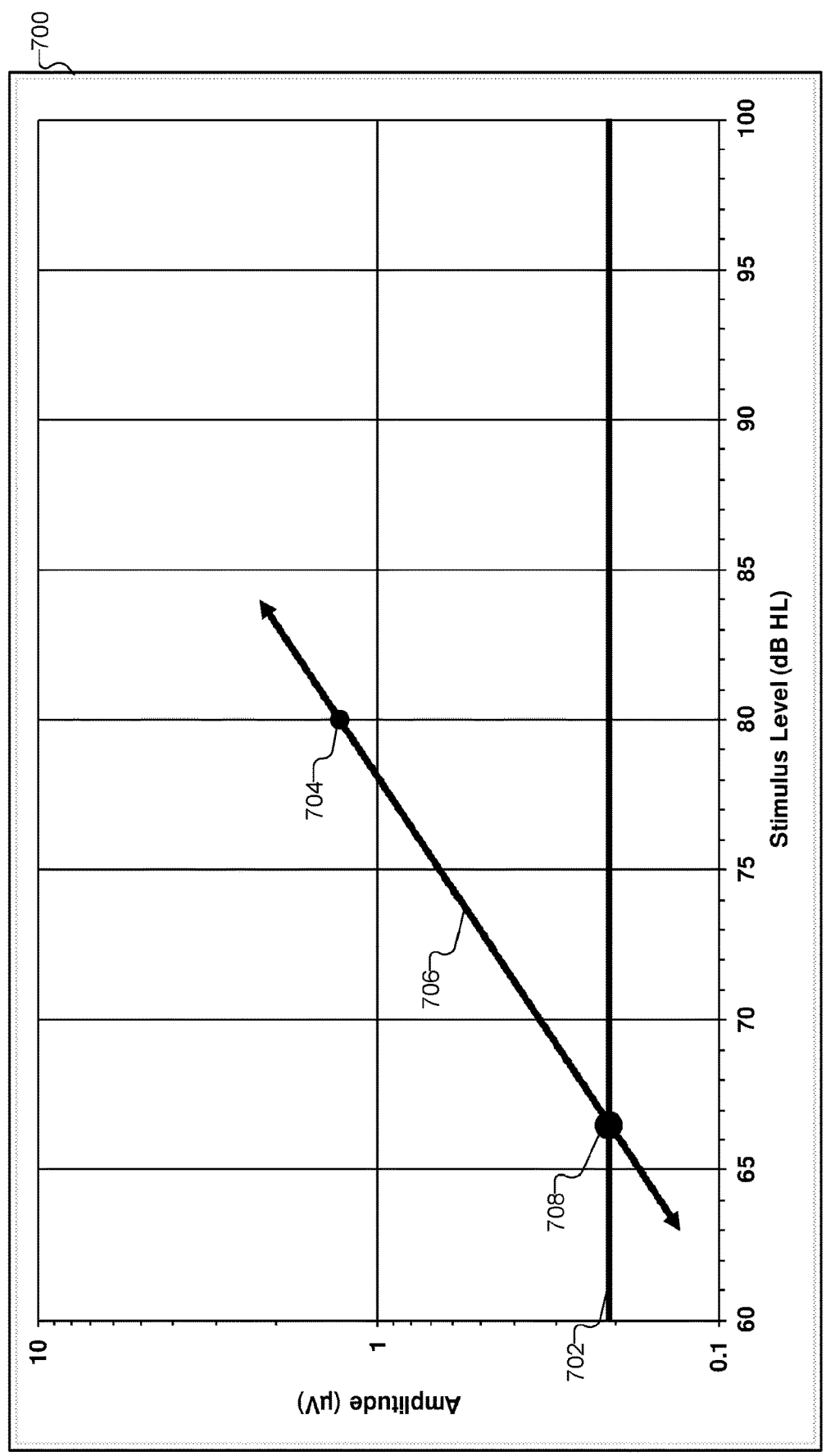
FIGS. 7-9 illustrate exemplary graphs according to principles described herein.

To illustrate, FIG. 7 shows an exemplary graph 700 of evoked response amplitudes measured in microvolts versus acoustic stimulation amplitudes (also referred to as "stimulus levels") in dB HL. In this particular example, management facility 602 has determined that the noise floor in the cochlea of a patient is approximately 0.21 μV. Line 702 in graph 700 represents the determined noise floor and is horizontal, indicating that the noise floor is presumed constant across all amplitudes of acoustic stimulation for the purposes of this example.

Continuing with this example, management facility 602 may apply acoustic stimulation having a predetermined frequency (e.g., 750 Hz) and a predetermined amplitude. In this particular example, the predetermined amplitude of the acoustic stimulation is 80 dB HL. As described above, management facility 602 may determine an amplitude of an evoked response that occurs in response to the acoustic stimulation at the predetermined amplitude. In this particular example, management facility 602 determines that the amplitude of the evoked response that occurs in response to the acoustic stimulation having a predetermined amplitude of 80 dB HL is approximately 1.3 µV. This value is represented in graph 700 by point 704.

To determine a behavioral audiogram value for the patient and that corresponds to the predetermined frequency of the acoustic stimulation used to elicit the evoked response, management facility 602 may use a linear approximation heuristic to identify a point within graph 700 where a line that intersects point 704 also intersects the line 702 that represents the noise floor. Such a line is illustrated in FIG. 7 by line 706. As shown, line 706 intersects the line 702 that represents the noise floor at an intersection point 708.

Management facility 602 may use the linear approximation heuristic to identify intersection point 708 in any suitable manner. For example, because a substantially linear relationship exists between amplitudes of acoustic stimuli that each have the same predetermined frequency and amplitudes of evoked responses that occur in response to the presented acoustic stimuli, the linear approximation heuristic may specify a predetermined slope of a line that is representative of the linear relationship. The value of the predetermined slope may be provided to management facility 602 (e.g., stored as part of behavioral audiogram data 606) and used by management facility 602 to define a line (i.e., line 706) that both intersects point 704 and has the predetermined slope.

In some examples, the predetermined slope used to define line 706 may be representative of an average linear relationship between evoked response amplitudes and acoustic stimulus amplitudes as measured across a plurality of patients. The predetermined slope may be class-specific (i.e., different for pediatric patients, adult patients, male patients, female patients, etc.). In some examples, management facility 602 may receive data representative of the predetermined slope from a user by way of a user interface.

Intersection point 708 represents an amplitude of acoustic stimulation having the predetermined frequency that elicits an evoked response that has an amplitude that is substantially at the noise floor represented by line 702. In other words, intersection point 708 may represent the lowest amplitude of sound that the patient can hear at the predetermined frequency. Hence, management facility 602 may designate a value corresponding to intersection point 708 as the behavioral audiogram value. In the example of FIG. 7, the value of intersection point 708 is approximately 66 dB HL. Hence, management facility 602 may designate 66 dB HL as the behavioral audiogram value corresponding to the predetermined frequency of the acoustic stimulation.

Additionally or alternatively, management facility 602 may determine the behavioral audiogram value using multiple stimulus amplitudes. In other words, management facility 602 may apply multiple instances of acoustic stimulation each having the same predetermined frequency, but having different predetermined amplitudes, in order to acquire information sufficient for determining the behavioral audiogram value. Use of multiple stimulation amplitudes may be beneficial, for example, when a predetermined slope is not available to management facility 602 or when use of a predetermined slope is not desirable for a particular patient.

Figure 8:
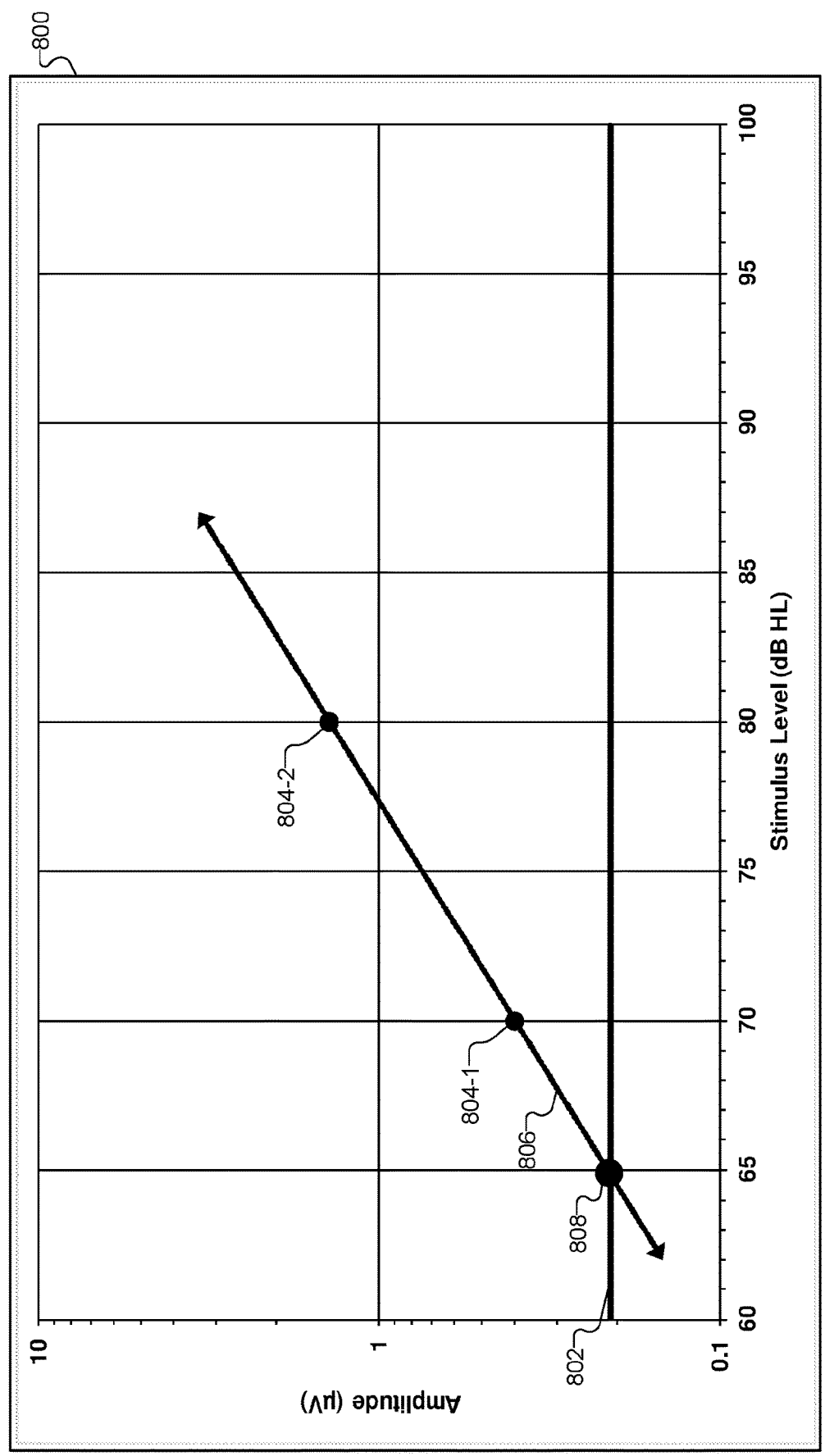

To illustrate, FIG. 8 shows an exemplary graph 800 of evoked response amplitudes measured in microvolts versus acoustic stimulation amplitudes in dB HL. As in FIG. 7, the determined noise floor in the cochlea of the patient is approximately 0.21 µV and is represented in graph 800 by line 802.

In this example, management facility 602 may apply a first instance of acoustic stimulation having a predetermined frequency (e.g., 750 Hz) and a predetermined amplitude of 70 dB HL. Management facility 602 may determine that an amplitude of an evoked response that occurs in response to this first instance of acoustic stimulation is approximately 0.4 µV. This value is represented in graph 800 by point 804-1. Management facility 602 may then apply a second instance of acoustic stimulation having the same predetermined frequency, but with a different predetermined amplitude of 80 dB HL. Management facility 602 may determine that an amplitude of an evoked response that occurs in response to this second instance of acoustic stimulation is approximately 1.4 µV. This value is represented in graph 800 by point 804-2.

Management facility 602 may then define a line that intersects both points 804-1 and 804-2. Such a line is illustrated in FIG. 8 by line 806, and may be defined by assigning a slope to the line that causes the line to intersect both points 804-1 and 804-2.

As shown, line 806 also intersects the line 802 that represents the noise floor at an intersection point 808. As described above, management facility 602 may designate intersection point 808 as the behavioral audiogram value corresponding to the predetermined frequency of the acoustic stimulation. For example, in FIG. 8, the value of intersection point 808 is approximately 65 dB HL. Hence, management facility 602 may designate 65 dB HL as the behavioral audiogram value corresponding to the predetermined frequency of the acoustic stimulation.

As another example of determining a behavioral audiogram value using multiple stimulus amplitudes, management facility 602 may determine a line of best fit among at least three points within a graph, wherein each of the at least three points is associated with a different stimulus amplitude.

Figure 9:
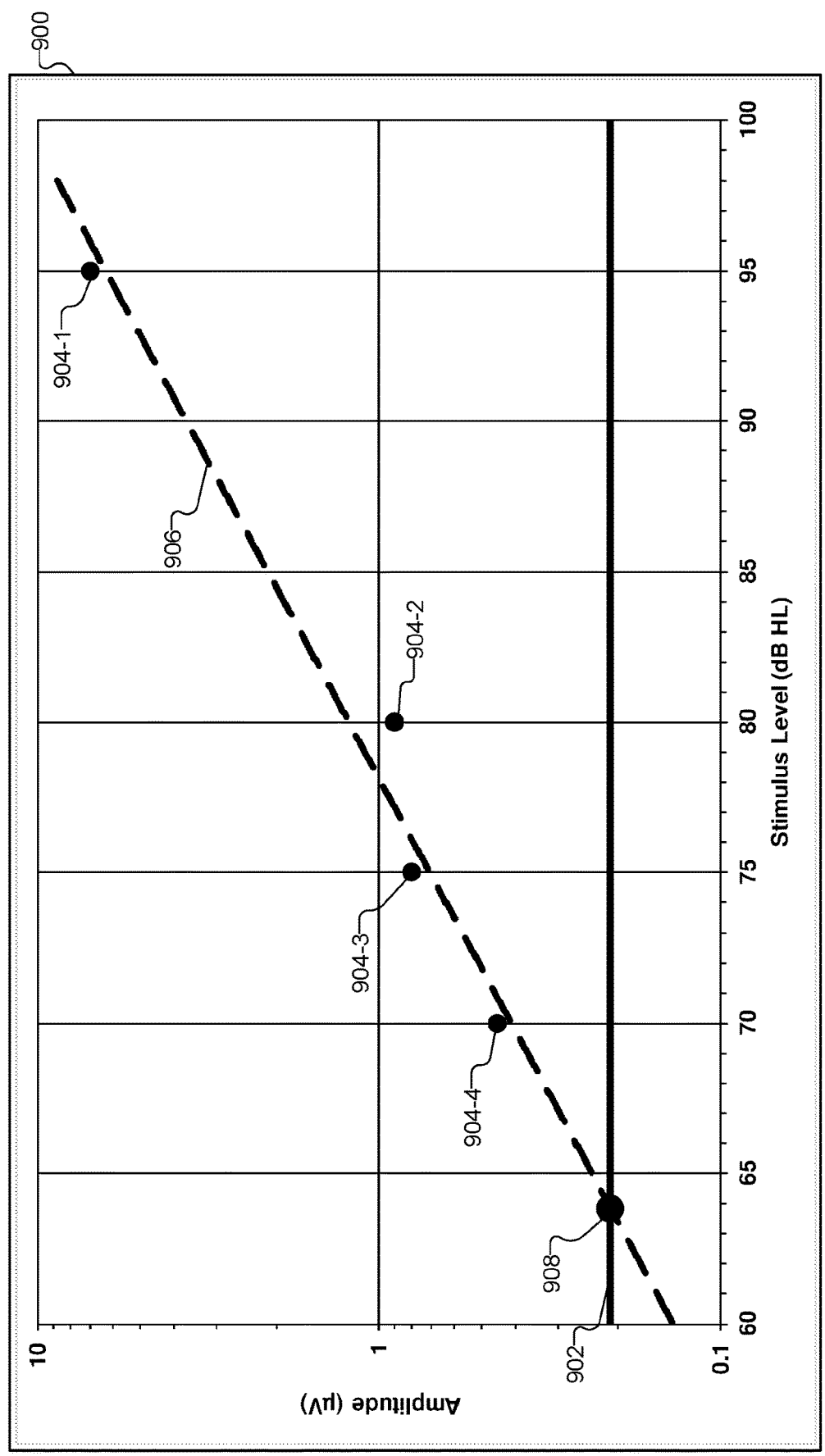

To illustrate, FIG. 9 shows an exemplary graph 900 of evoked response amplitudes measured in microvolts versus acoustic stimulation amplitudes in dB HL. As in FIGS. 7 and 8, the determined noise floor in the cochlea of the patient is approximately 0.21 µV and is represented in graph 900 by line 902.

In this example, management facility 602 may apply four instances of acoustic stimulation each having a predetermined frequency (e.g., 750 Hz), but different predetermined amplitudes. Management facility 602 may, in any of the ways described herein, determine the amplitudes of the various evoked responses that occur in response to the four instances of acoustic stimulation. The determined amplitudes are represented in graph 900 by points 904-1 through 904-4 (collectively "points 904").

Management facility 602 may then determine a line of best fit among the four points 904. This line of best fit is represented in FIG. 9 by line 906. Management facility 602 may determine the line of best fit in any way as may serve a particular implementation. As an example, management facility 602 may use a Least Squares Method ("LSM") to determine the line of best fit among the four points 904. As shown, the line of best fit 906 may not precisely intersect one or more of points 904.

As shown, line 906 intersects the line 902 that represents the noise floor at an intersection point 908. As described above, management facility 602 may designate intersection point 908 as the behavioral audiogram value corresponding to the predetermined frequency of the acoustic stimulation. For example, in FIG. 9, the value of intersection point 908 is approximately 64 dB HL. Hence, management facility 602 may designate 64 dB HL as the behavioral audiogram value corresponding to the predetermined frequency of the acoustic stimulation.

The above-described processes for determining a behavioral audiogram value corresponding to a particular frequency may be repeated for a plurality of frequencies (e.g., frequencies commonly included in a behavioral audiogram). Management facility 602 may then generate an overall behavioral audiogram for the patient based on the individual behavioral audiogram values determined for each individual frequency. This may be performed in any suitable manner. For example, management facility 602 may use the individual behavioral audiogram values to generate and display a graph representative of the behavioral audiogram for the patient.

In some examples, management facility 602 may concurrently present multiple instances of acoustic stimulation each having the same amplitude, but with different predetermined frequencies. This concurrent presentation of acoustic stimulation may concurrently elicit evoked responses for each predetermined frequency. The amplitudes of these evoked responses may be determined by management facility 602 and used to concurrently determine behavioral audiogram values for each of the predetermined frequencies. This may reduce the amount of time it takes to generate a behavioral audiogram for a particular patient.

Figure 10:
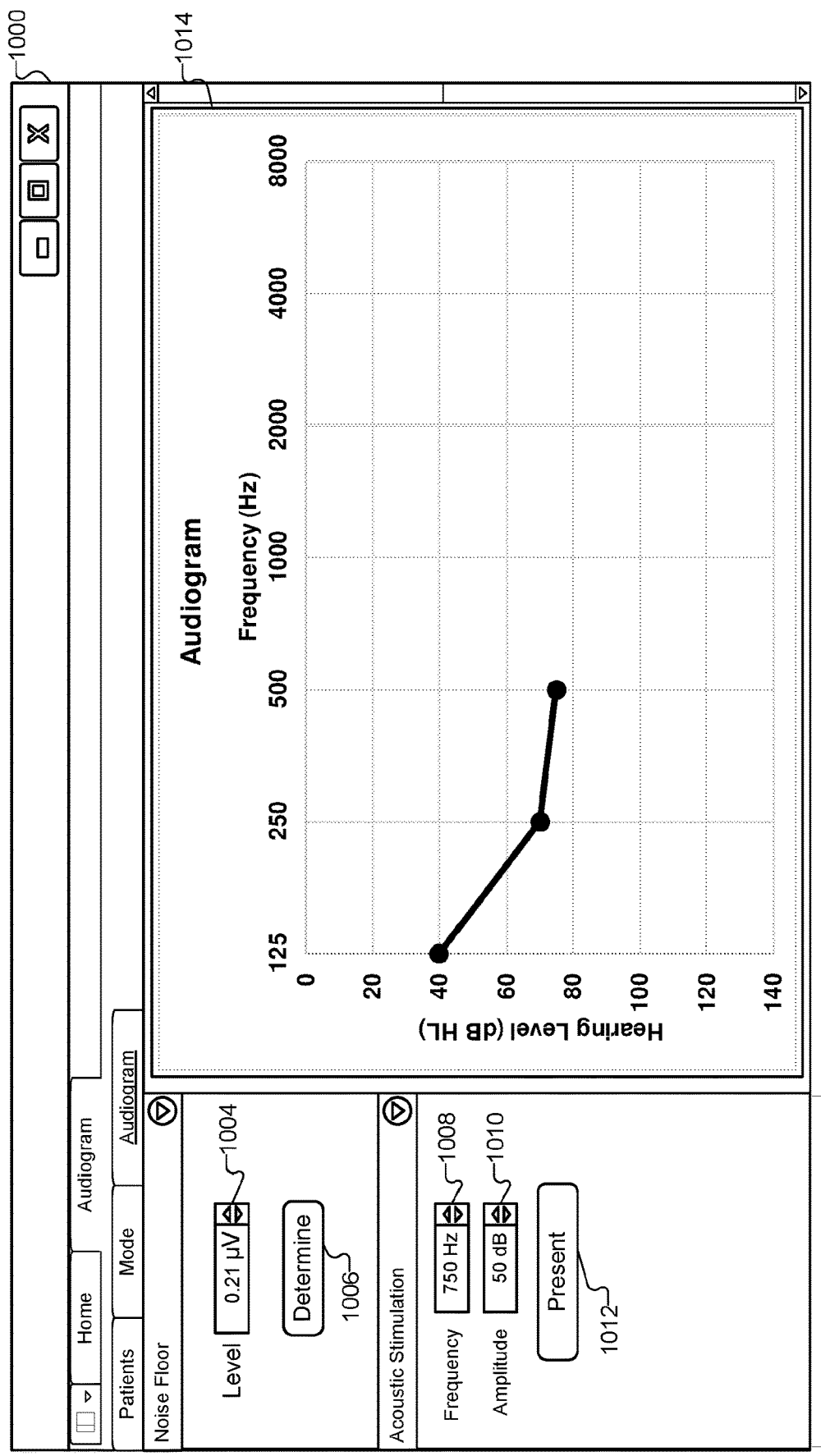
FIG. 10 shows an exemplary graphical user interface according to principles described herein.

FIG. 10 shows an exemplary graphical user interface that management facility 602 may display to facilitate user interaction with system 600 (e.g., by way of a display screen included in or connected to programming system 402).

FIG. 10 shows an exemplary behavioral audiogram management GUI 1000 ("GUI 1000") that may be displayed by management facility 602. A user may interact with various options shown in pane 1002 to direct management facility 602 to perform one or more of the operations described herein. For example, a user may interact with spinner 1004 to enter a noise floor value for the cochlea of the patient. Additionally or alternatively, the user may select button 1006 to direct management facility 602 to determine the noise floor within the cochlea of the patient in any of the ways described herein.

The user may also interact with GUI 1000 to define one or more attributes (e.g., amplitude and/or frequency) of an acoustic stimulation and to direct management facility 602 to present the acoustic stimulation to the patient. The user may interact with spinners 1008 and 1010 to select attributes of an acoustic stimulation that management facility 602 may present to the patient. For example, the user may interact with spinner 1008 to enter a frequency for the acoustic stimulation, and spinner 1010 to enter an amplitude for the acoustic stimulation. Having set the noise floor and the attributes of the acoustic stimulation, the user may then select button 1012 to direct management facility 602 to present the acoustic stimulation to the user.

Management facility 602 may then determine a behavioral audiogram value for the patient that corresponds to the frequency and generate and display a behavioral audiogram for the patient according to principles described herein. To illustrate, GUI 1000 shows an exemplary behavioral audiogram 1014 for the patient and that includes behavioral audiogram values corresponding to frequencies of 125 Hz, 250 Hz, and 500 Hz. Upon selection of button 1012, management facility 602 will update behavioral audiogram 1014 to include a behavioral audiogram value corresponding to a frequency of 750 Hz.

It will be recognized that other GUIs may be presented to the user as may serve a particular implementation. For example, a GUI may be presented to the user that allows the user to direct management facility 602 to concurrently present multiple instances of acoustic stimulation to the patient.

Figure 11:
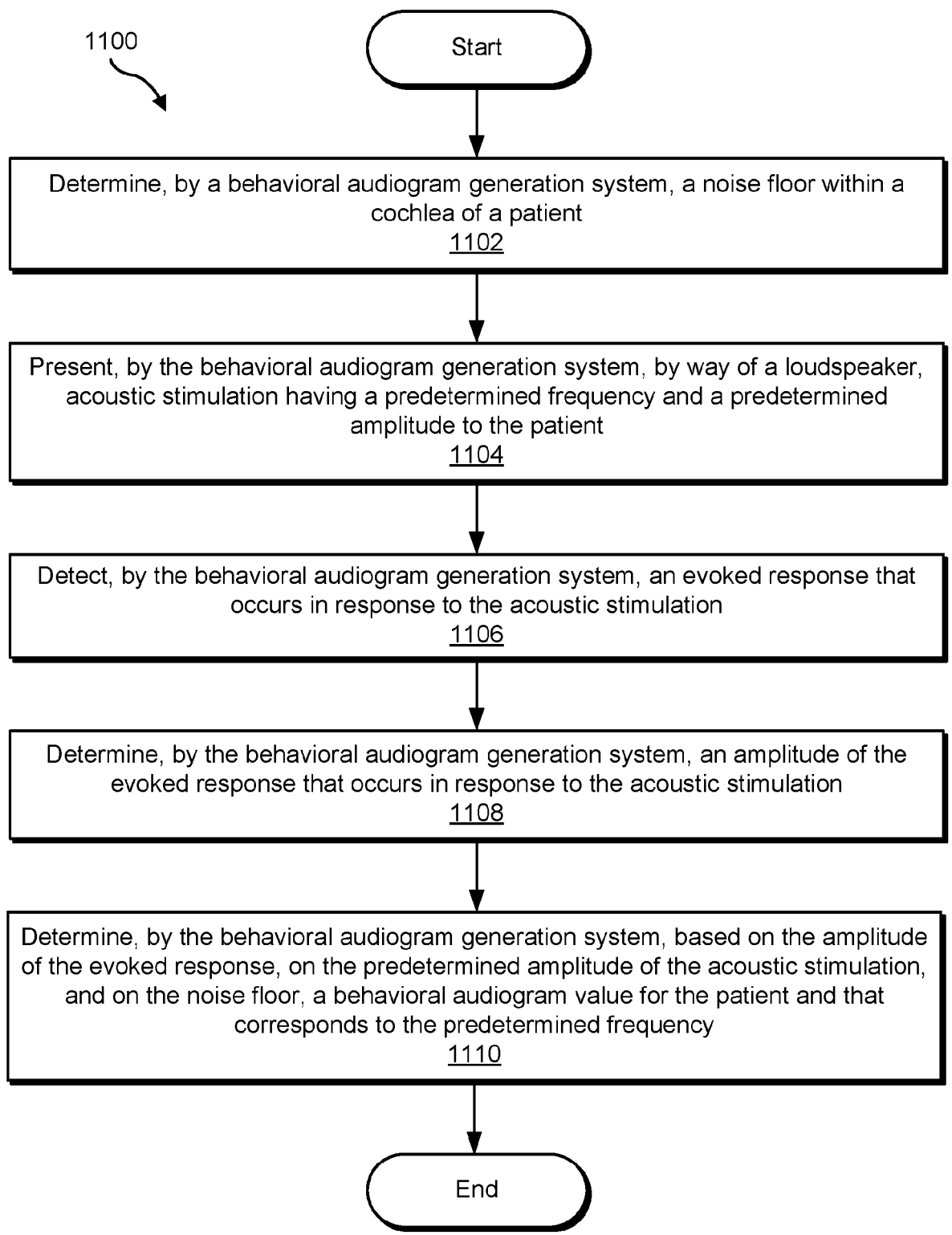
FIG. 11 illustrates operations of an exemplary method for using detected evoked responses to determine behavioral audiogram values according to principles described herein.

FIG. 11 illustrates an exemplary method 1100 of using detected evoked responses to determine behavioral audiogram values. While FIG. 11 illustrates exemplary steps according to one embodiment, other embodiments may omit, add to, reorder, and/or modify any of the operations shown in FIG. 11. One or more of the operations shown in FIG. 11 may be performed by behavioral audiogram generation system 600 and/or any implementation thereof.

In operation 1102, a behavioral audiogram generation system determines a noise floor within a cochlea of a patient. Operation 1102 may be performed in any of the ways described herein.

In operation 1104, the behavioral audiogram generation system presents, by way of a loudspeaker, acoustic stimulation having a predetermined frequency and a predetermined amplitude to the patient. Operation 1104 may be performed in any of the ways described herein.

In operation 1106, the behavioral audiogram generation system detects an evoked response that occurs in response to the acoustic stimulation. Operation 1106 may be performed in any of the ways described herein.

In operation 1108, the behavioral audiogram generation system determines an amplitude of the evoked response that occurs in response to the acoustic stimulation. Operation 1108 may be performed in any of the ways described herein.

In operation 1110, the behavioral audiogram generation system determines, based on the amplitude of the evoked response, on the predetermined amplitude of the acoustic stimulation, and on the noise floor, a behavioral audiogram value for the patient and that corresponds to the predetermined frequency. Operation 1110 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), erasable programmable read-only memory ("EPROM"), electrically erasable programmable read-only memory ("EEPROM"), a Flash EEPROM device, any other memory chip or cartridge, or any other tangible medium from which a computer can read.

Figure 12:
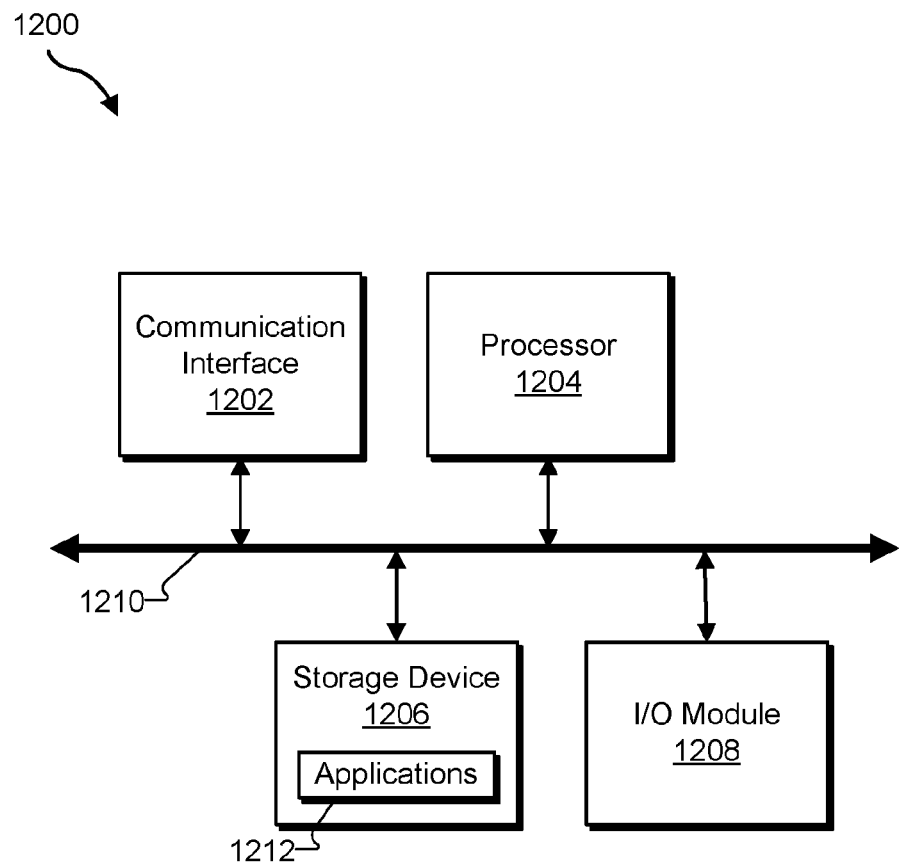
FIG. 12 illustrates an exemplary computing device according to principles described herein.

FIG. 12 illustrates an exemplary computing device 1200 that may be specifically configured to perform one or more of the processes described herein. As shown in FIG. 12, computing device 1200 may include a communication interface 1202, a processor 1204, a storage device 1206, and an input/output ("I/O") module 1208 communicatively connected via a communication infrastructure 1210. While an exemplary computing device 1200 is shown in FIG. 12, the components illustrated in FIG. 12 are not intended to be limiting. Additional or alternative components may be used in other embodiments. Components of computing device 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, an audio/video connection, and any other suitable interface.

Processor 1204 generally represents any type or form of processing unit capable of processing data or interpreting, executing, and/or directing execution of one or more of the instructions, processes, and/or operations described herein. Processor 1204 may direct execution of operations in accordance with one or more applications 1212 or other computer-executable instructions such as may be stored in storage device 1206 or another computer-readable medium.

Storage device 1206 may include one or more data storage media, devices, or configurations, and may employ any type, form, and combination of data storage media and/or device. For example, storage device 1206 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1206. For example, data representative of one or more executable applications 1212 configured to direct processor 1204 to perform any of the operations described herein may be stored within storage device 1206. In some examples, data may be arranged in one or more databases residing within storage device 1206.

I/O module 1208 may be configured to receive user input and provide user output and may include any hardware, firmware, software, or combination thereof supportive of input and output capabilities. For example, I/O module 1208 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1200. For example, one or more applications 1212 residing within storage device 1206 may be configured to direct processor 1204 to perform one or more processes or functions associated with management facility 602. Likewise, storage facility 604 may be implemented by or within storage device 1206.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
    at least one physical computing device that
    determines a noise floor within a cochlea of a patient;
    presents, by way of a loudspeaker, acoustic stimulation having a predetermined frequency and a predetermined amplitude to the patient;
    detects an evoked response that occurs in response to the acoustic stimulation;
    determines an amplitude of the evoked response that occurs in response to the acoustic stimulation; and
    determines, based on the amplitude of the evoked response, on the predetermined amplitude of the acoustic stimulation, and on the noise floor, a behavioral audiogram value for the patient and that corresponds to the predetermined frequency, the behavioral audiogram value representing a lowest amplitude at which the patient is able to detect a presentation of a tone having the predetermined frequency.

2. The system of claim 1, wherein the at least one physical computing device further generates, based on the behavioral audiogram value, a behavioral audiogram for the patient.

3. The system of claim 1, wherein the at least one physical computing device further:
    detects at least one additional evoked response that occurs in response to the acoustic stimulation; and
    adjusts, based on an average signal-to-noise ratio of the detected evoked response and the detected at least one additional evoked response, the determined noise floor.

4. The system of claim 1, wherein the at least one physical computing device comprises a sound processor included in an electro-acoustic stimulation ("EAS") system, wherein the sound processor is physically and communicatively coupled to the loudspeaker, and wherein the sound processor:
    presents the acoustic stimulation by way of the loudspeaker that is physically and communicatively coupled to the sound processor; and detects the evoked response that occurs in response to the presented acoustic stimulation by wirelessly receiving a signal representative of the evoked response by way of a cochlear implant included in the EAS system.

5. The system of claim 1, wherein the at least one physical computing device comprises a programming device that is communicatively coupled to a sound processor included in a cochlear implant system associated with the patient and that is physically and communicatively coupled to the loudspeaker, and wherein the programming device:
presents the acoustic stimulation by way of the loudspeaker that is physically and communicatively coupled to the programming device, and
detects the evoked response that occurs in response to the presented acoustic stimulation by receiving a signal representative of the evoked response from the sound processor.

6. The system of claim 1, wherein the at least one physical computing device determines the noise floor by:
abstaining from presenting any acoustic stimulation to the patient for a predetermined time period;
using an electrode implanted within the patient to record a signal while the at least one physical computing device abstains from presenting any acoustic stimulation during the predetermined time period;
determining an amplitude of the recorded signal; and
designating the determined amplitude of the recorded signal as the noise floor.

7. The system of claim 1, wherein the at least one physical computing device determines the noise floor by receiving data representative of the noise floor from a source external to the at least one physical computing device.

8. The system of claim 1, wherein the at least one physical computing device determines the behavioral audiogram value by:
using a linear approximation heuristic to identify a first point, in a graph of evoked response amplitudes versus acoustic stimulation amplitudes, where a first line intersects a second line representative of the noise floor; and
designating a value corresponding to the identified first point as the behavioral audiogram value.

9. The system of claim 8, wherein the first line also intersects a second point representative of the amplitude of the evoked response at the predetermined amplitude of the acoustic stimulation.

10. The system of claim 9, wherein the at least one physical computing device defines the first line in accordance with the second point and a predetermined slope.

11. The system of claim 10, wherein the at least one physical computing device receives data representative of the predetermined slope from a source external to the at least one physical computing device.

12. The system of claim 8, wherein the at least one physical computing device defines the first line by:
identifying a second point representative of the amplitude of the evoked response at the predetermined amplitude of the acoustic stimulation;
presenting, by way of the loudspeaker, an additional acoustic stimulation having the predetermined frequency and an additional predetermined amplitude to the patient;
detecting an additional evoked response that occurs in response to the additional acoustic stimulation;
determining an additional amplitude of the additional evoked response that occurs in response to the additional acoustic stimulation; and
assigning a slope to the first line that causes the first line to intersect both the second point and a third point representative of the additional amplitude of the additional evoked response at the additional predetermined amplitude of the additional acoustic stimulation.

13. The system of claim 8, wherein the at least one physical computing device defines the first line by:
identifying a second point representative of the amplitude of the evoked response at the predetermined amplitude of the acoustic stimulation;
presenting, by way of the loudspeaker, at least two additional acoustic stimulations having the predetermined frequency and at least two additional predetermined amplitudes to the patient;
detecting at least two additional evoked responses that occur in response to the at least two additional acoustic stimulations;
determining at least two additional amplitudes of the at least two additional evoked responses that occur in response to the at least two additional acoustic stimulations;
determining a line of best fit among the second point and at least two additional points representative of the at least two additional amplitudes of the at least two additional evoked responses at the at least two predetermined amplitudes of the at least two additional acoustic stimulations; and
designating the determined line as the first line.

14. The system of claim 1, wherein the at least one physical computing device further:
presents, by way of the loudspeaker, a second acoustic stimulation having a second predetermined frequency and a second predetermined amplitude to the patient;
detects a second evoked response that occurs in response to the second acoustic stimulation;
determines a second amplitude of the second evoked response that occurs in response to the second acoustic stimulation; and
determines, based on the second amplitude of the second evoked response, on the second predetermined amplitude of the second acoustic stimulation, and on the noise floor, a second behavioral audiogram value for the patient and that corresponds to the second predetermined frequency.

15. The system of claim 1, wherein the at least one physical computing device further:
presents, by way of the loudspeaker, concurrently with the presentation of the acoustic stimulation, a second acoustic stimulation having a second predetermined frequency and the predetermined amplitude to the patient;
detects, concurrently with the detection of the evoked response, a second evoked response that occurs in response to the second acoustic stimulation;
determines a second amplitude of the second evoked response that occurs in response to the second acoustic stimulation; and
determines, based on the amplitude of the second evoked response, on the second predetermined amplitude of the second acoustic stimulation, and on the noise floor, a second behavioral audiogram value for the patient and that corresponds to the second predetermined frequency.

16. The system of claim 1, wherein the noise floor comprises a predetermined threshold value that is not representative of an actual noise floor within the cochlea of the patient.

17. A system comprising:
at least one physical computing device that
- determines a noise floor within a cochlea of a patient;
- detects an evoked response that occurs in response to acoustic stimulation having a predetermined frequency and a predetermined amplitude;
- determines an amplitude of the evoked response that occurs in response to the acoustic stimulation; and
- determines, based on the amplitude of the evoked response, on the predetermined amplitude of the acoustic stimulation, and on the noise floor, a behavioral audiogram value for the patient and that corresponds to the predetermined frequency by:
  - using a linear approximation heuristic to identify a first point, in a graph of evoked response amplitudes versus acoustic stimulation amplitudes, where a first line intersects a second line representative of the noise floor, the first line also intersecting a second point representative of the amplitude of the evoked response at the predetermined amplitude of the acoustic stimulation, and
  - designating a value corresponding to the first point as the behavioral audiogram value, the behavioral audiogram value representing a lowest amplitude at which the patient is able to detect a presentation of a tone having the predetermined frequency.

18. The system of claim 17, wherein the at least one physical computing device comprises a sound processor included in an electro-acoustic stimulation ("EAS") system, wherein the sound processor is physically and communicatively coupled to the loudspeaker, and wherein the sound processor:
- presents the acoustic stimulation by way of the loudspeaker that is physically and communicatively coupled to the sound processor; and
- detects the evoked response that occurs in response to the presented acoustic stimulation by wirelessly receiving a signal representative of the evoked response by way of a cochlear implant included in the EAS system.

19. The system of claim 17, wherein the at least one physical computing device comprises a programming device that is communicatively coupled to a sound processor included in a cochlear implant system associated with the patient and that is physically and communicatively coupled to the loudspeaker, and wherein the programming device:
- presents the acoustic stimulation by way of the loudspeaker that is physically and communicatively coupled to the programming device, and
- detects the evoked response that occurs in response to the presented acoustic stimulation by receiving a signal representative of the evoked response from the sound processor.

20. A method comprising:
- determining, by a behavioral audiogram generation system, a noise floor within a cochlea of a patient;
- presenting, by the behavioral audiogram generation system, by way of a loudspeaker, acoustic stimulation having a predetermined frequency and a predetermined amplitude to the patient;
- detecting, by the behavioral audiogram generation system, an evoked response that occurs in response to the acoustic stimulation;
- determining, by the behavioral audiogram generation system, an amplitude of the evoked response that occurs in response to the acoustic stimulation; and
- determining, by the behavioral audiogram generation system, based on the amplitude of the evoked response, on the predetermined amplitude of the acoustic stimulation, and on the noise floor, a behavioral audiogram value for the patient and that corresponds to the predetermined frequency, the behavioral audiogram value representing a lowest amplitude at which the patient is able to detect a presentation of a tone having the predetermined frequency.

\* \* \* \* \*